US 6,683,276 B2

(12) United States Patent
Mosavi

(10) Patent No.: US 6,683,276 B2
(45) Date of Patent: Jan. 27, 2004

(54) METHOD OF FORMING CHAMFERED BLIND HOLES IN SURGICAL NEEDLES USING A DIODE PUMPED ND-YAG LASER

(75) Inventor: Reza K. Mosavi, Alto, GA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 10/235,374

(22) Filed: Sep. 5, 2002

(65) Prior Publication Data
US 2003/0111448 A1 Jun. 19, 2003

Related U.S. Application Data

(63) Continuation-in-part of application No. 09/864,035, filed on May 23, 2001, which is a continuation of application No. 09/298,876, filed on Apr. 26, 1999, now Pat. No. 6,252,195.

(51) Int. Cl.$^7$ ................................................. B23K 26/38
(52) U.S. Cl. ................................................. 219/121.71
(58) Field of Search ................... 219/121.67, 121.7, 219/121.71, 121.72, 121.85

(56) References Cited

U.S. PATENT DOCUMENTS

| 4,808,789 A | | 2/1989 | Muncheryan |
| 4,910,377 A | | 3/1990 | Matsutani et al. |
| 5,012,066 A | | 4/1991 | Matsutani et al. |
| 5,059,764 A | | 10/1991 | Baer |
| 5,477,604 A | * | 12/1995 | Smith et al. |
| 5,889,255 A | | 3/1999 | Bogart et al. |

FOREIGN PATENT DOCUMENTS

| GB | 1 424 953 A | 2/1976 |
| JP | 63-140789 A | 6/1988 |

* cited by examiner

Primary Examiner—Samuel M. Heinrich
(74) Attorney, Agent, or Firm—Emil Richard Skula

(57) ABSTRACT

A method of laser drilling surgical needles. The method utilizes a diode pulsed laser to produce a laser beam consisting of a train of high energy pulses. The method produces laser drilled chamfered blind bore holes in surgical needles.

8 Claims, 7 Drawing Sheets

FIG. 1 *Prior Art*

Penta-Pulse Temporal Profile

Time (microseconds)

Pulse Width= 50 µs    Pulse Energy= 50 µJ

Dual Pulse Temporal Profile

Time (microseconds)

Pulse Width= 50 µs    Pulse Energy= 50 µJ

METHOD OF FORMING CHAMFERED BLIND HOLES IN SURGICAL NEEDLES USING A DIODE PUMPED ND-YAG LASER

This is a continuation-in-part of commonly-assigned U.S. patent application Ser. No. 09/864,035 filed on May 23, 2001 which is a continuation of U.S. patent application Ser. No. 09/298,876 filed on Apr. 26, 1999, now U.S. Pat. No. 6,252,195B1.

TECHNICAL FIELD

The field of art to which this invention relates is surgical needles, in particular, a method of drilling and forming chamfered blind holes in surgical needles using lasers.

BACKGROUND OF THE INVENTION

Surgical needles and attached sutures are well known in the art. Surgical needles typically have a distal pointed end and a proximal suture mounting end. The suture mounting end can have several structural configurations for receiving a suture tip, including channels and blind holes. The distal end of a suture is typically mounted to the proximal end of a surgical needle in several ways. For example the distal end or tip of the suture may be inserted into a channel, and the channel is then mechanically swaged to lock the suture in the channel. Or, the distal end or tip of a suture may be mounted into a bore hole drilled into the proximal end of a needle. The proximal end of the needle is then mechanically swaged such that the suture end is mechanically locked into the bore hole. Alternatively, sutures may be mounted to surgical needles using adhesives, epoxies, shrink tubing and other known mounting techniques.

The use of blind bore holes to mount sutures to surgical needles has become the mounting method of choice for many types of surgical needles. The needles having suture mounted in this manner may have less resistance to penetration when moved through tissue. Blind bore holes are typically drilled into the proximal ends of needles using one of two conventional methods. One method of drilling surgical needles is to use mechanical drills. The other method of drilling blind bore holes is to use lasers. Mechanical drilling is known to have several disadvantages including mechanical alignment, tool wear, constant adjustments, the inability to drill small diameter holes, and relative slowness of the mechanical drilling process. The use of laser drilling overcomes many of these problems. The laser uses a beam of light energy to form the blind bore hole by liquifying the metal and causing it to be expelled from the proximal end of the needle. Accordingly, in laser drilling there is no mechanical contact with needle by the drilling apparatus, tool wear is not a problem, alignment problems and adjustments are minimized, and drilling is considerably more time effective, allowing for high production throughput.

Although the use of conventional laser systems to drill surgical needles has many advantages, there are also some problems which are attendant with their use. Laser drilling equipment is typically more sophisticated and complex than mechanical drilling equipment and requires highly skilled operators. In addition, the laser drilling may produce a bore hole which does not have an entirely smooth interior surface because of residual slag resulting from the expulsion of the molten metal. The slag may interfere with the insertion of a suture into a bore hole.

It is known that to produce a smooth bore hole it is desirable to remove metal from a bore hole through evaporation and plasma formation rather than a melting process. This can be done by using pulsed Nd-YAG lasers. Such lasers produce a train of short pulses having sufficient energy to remove small amounts of material with each pulse, thereby producing a high quality bore hole. The duration of the pulses is typically in the 10 microseconds to 100 micro seconds range.

Presently, short pulses for drilling surgical needles are produced using a conventional flash lamp pumped Nd-YAG laser as an oscillator to produce an optical pulse range from 200 microseconds to 600 microseconds duration. This optical pulse is then intensity modulated by an electro-optical modulator or similar device into a plurality of short pulses (i.e., a pulse train). The duration of these short pulses and their frequencies are controlled by the modulator parameters. The pulse train then enters a conventional flash lamp pumped Nd-YAG amplifier and is amplified to produce a high power intensity beam. The high power intensity beam is then focused on the rear or proximal end face of a surgical needle to drill a blind hole into the proximal end of the needle.

Because of the inherent limitations of flash lamp pulsing, the production of short pulses requires modulation of the main pulse by means of an electro-optical modulator, which in turn requires an optical polarizer and analyzer. The addition of these optical devices along the path of the laser beam causes the loss of some optical energy, and is associated with some difficulty in keeping the optical devices optically aligned in the manufacturing environment. The electro-optical modulator (Pockles Cell) requires the use of high voltage electronics which in turn require high maintenance and extensive safety precautions. The flash lamp pumped laser oscillator and amplifier use both high voltage power supplies and capacitor banks to store energy for discharging into the flash lamp. The flash lamp is believed to be an inefficient way of pumping a laser rod, since most of the energy is dissipated in the form of heat which must be removed by a cooling system. The power supply, capacitor banks, and cooling system require significant amounts of space, maintenance and troubleshooting. The heat dissipated in the laser rod from flash lamp operation also causes thermal lensing of the rod, which deteriorates the quality of the laser beam. Another problem observed with the existing flash lamp pumped method is usable flash lamp life. The average flash lamp may have a life of about 500 to 600 hours. This requires shutting down the laser drilling system every 600 or so hours to replace the flash lamp thereby interrupting production, and necessitating maintenance and repair.

It is also known in this art to provide drilled bore holes that are chamfered. The chamfering of surgical needle bore holes is believed to enhance the efficiency and efficacy of the attachment of surgical sutures to surgical needles when the distal ends of the sutures are placed into the bore holes. Chamfering of surgical needles is conventionally performed by mechanical machining with machine tools, or by using two laser systems. In a chamfered hole the diameter of the chamfer is larger than the diameter of the bore hole. This enhances and facilitates the insertion of a distal end of a suture into a drilled bore hole, and also has the effect of reducing suture clip-off adjacent to the needle attachment point due to suture flexion during surgery. A chamfer is produced in a mechanical drilling process by initially machining the chamfer or counter-sink, and then drilling the bore hole. Two separate bits are used in the machining process. When producing a chamfered drilled bore hole using a laser process, two separate lasers are employed. One laser drills the bore hole into the needle. The other laser is used to drill the chamfer. The laser processes are believed to be advantageous over the mechanical processes for a number or reasons. For example, laser systems eliminate the need for contact with a mechanical tool, there is no tool wear, the throughput of the laser process is much higher. However, the use of two lasers in a system to drill chamfered holes can be complicated, bulky and not optimally cost efficient.

Although the laser systems known in the art are satisfactory to produce drilled chamfered bore holes in surgical needles, there is a need in this art for novel laser systems having improved characteristics.

Accordingly, there is a need in this art for improved pulsed laser systems which overcome the disadvantages of a flash lamp pulsing system and which provide blind bore holes having chamfering. There is a need for a novel laser system and process that can produce drilled chamfered bore holes in surgical needles using a single laser.

SUMMARY OF THE INVENTION

Therefore, it is an object of the present invention to provide a method of pulsed laser drilling of surgical needles which is efficient, and which eliminates the need for an optical polarizer, an electro-optical modulator, an analyzer, a flash lamp and associated power supplies and capacitor banks.

It is also an object of the present invention to provide for a pulsed laser drilling system which is easier to cool, which has reduced heating of the laser rod and reduced thermal lensing effect, and which can operate significantly longer than a flash lamp pumped system without having downtime.

It is yet another object of the present invention to provide a method of pulsed laser drilling of surgical needles using a single laser to produced chamfered drilled bore holes.

Accordingly, a method of laser pulsed drilling of surgical needles is disclosed. The method consists of providing a laser drilling apparatus which utilizes an oscillator consisting of an Nd-YAG crystal rod and a plurality of high power laser diode arrays. An optical pulse is produced by the laser apparatus. The pulse is focused on the proximal end of a surgical needle to make a blind hole.

Yet another aspect of the present invention is a method of laser drilling chamfered bore holes in surgical needles. In this method, a laser drilling apparatus is provided which utilizes an oscillator consisting of an Nd-Yag crystal rod and a plurality of high power laser diode arrays. A first optical pulse is produced by the laser drilling apparatus and focused on the proximal end of a surgical needle to create a chamfered cavity. A second optical pulse is produced by the same laser apparatus and focused on the proximal end of the surgical needle to produce a drilled blind hole. The processed needle has a chamfered blind hole drilled by a single laser drilling apparatus. The laser drilling apparatus is controlled by a central processing unit consisting of at least one programmable microprocessor.

These and other advantages of the present invention will become more apparent from the following description and accompanying drawings.

DETAILED DESCRIPTION OF THE PREFERRED EMBODIMENTS

Figure 1:
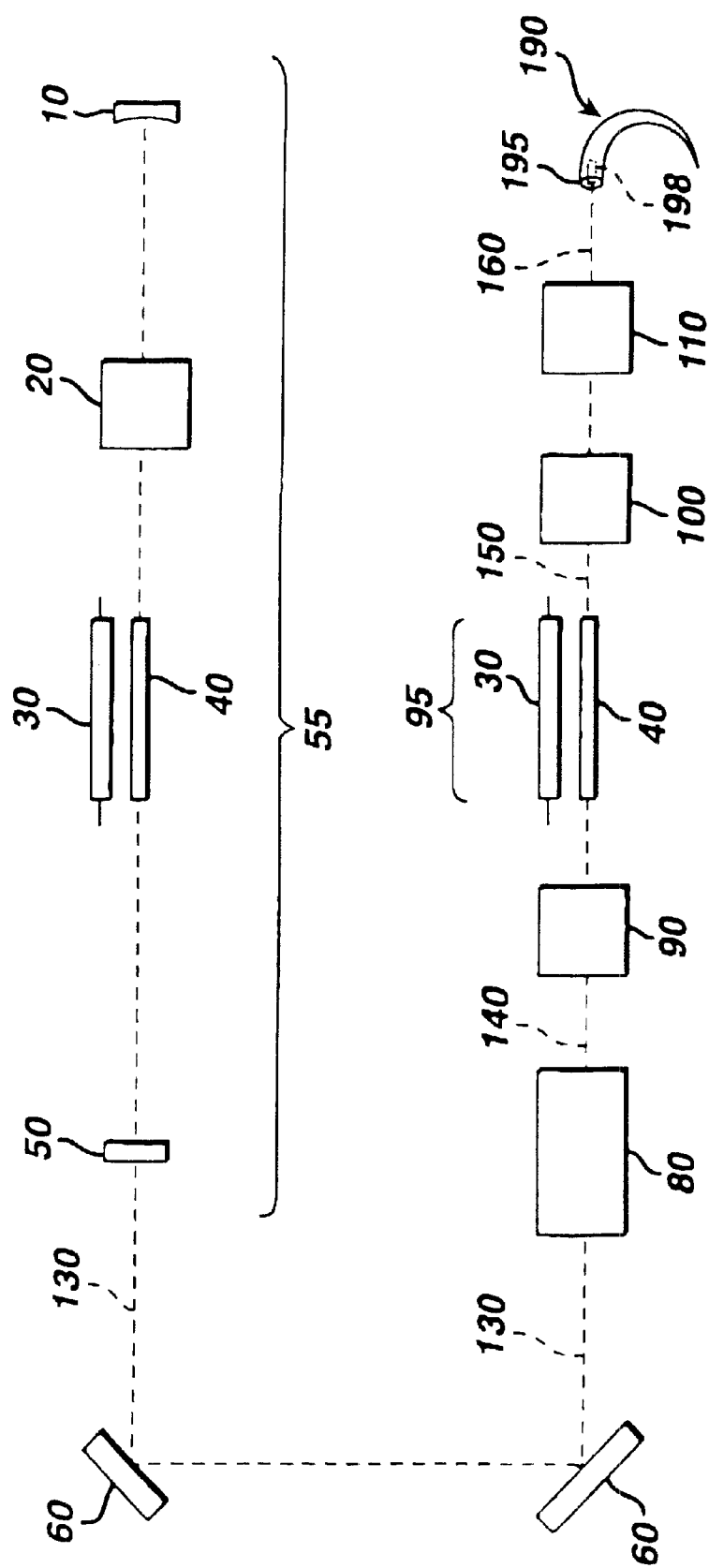
FIG. 1 is a schematic diagram of a flash lamp pulsed laser drilling system of the prior art.
Figure 2:
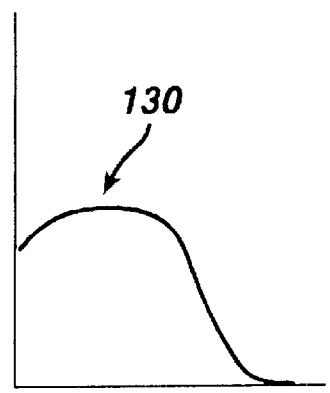
FIG. 2 is a schematic diagram of a typical optical pulse produced by a flash lamp pumped Nd-YAG laser oscillator of the prior art.
Figure 3:
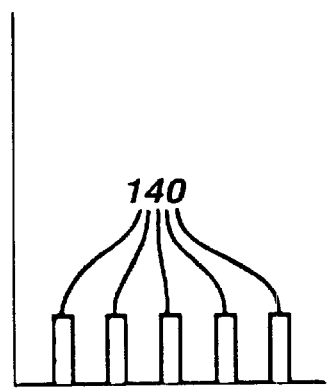
FIG. 3 is a schematic diagram illustrating a typical train of pulses created by modulating the single optical pulse of FIG. 2.
Figure 4:
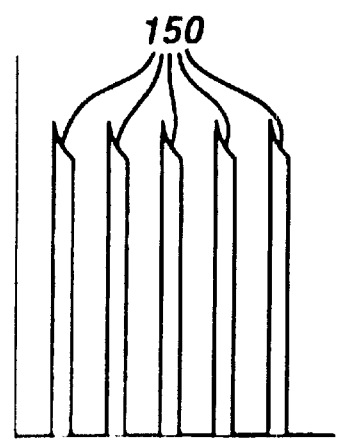
FIG. 4 is a schematic view showing the train of pulses of FIG. 3 after amplification.

A schematic diagram of a flash lamp pumped Nd-YAG laser drilling system of the prior art is illustrated in FIG. 1. As seen in FIG. 1, the system has a rear, convex 100% reflective mirror 10 aligned with a beam polarizer 20, and an Nd-YAG laser rod 40. Adjacent to the Nd-YAG laser rod 40 is a flash lamp 30. Aligned with laser rod 40 is an output coupler mirror 50. The combination of the mirror 10, the beam polarizer 20, the flash lamp 30, the laser rod 40, and the output coupler mirror 50 comprises the laser oscillator 55. The flash lamp 30 pumps the Nd-YAG rod 40 into a higher energy level, and the mirrors 10 and 50 cause the laser oscillation to occur. The beam polarizer 20 linearly polarizes the laser beam. An optical pulse 130, as illustrated in FIG. 2, then exits the output coupler mirror 50 and reflects sequentially off of a pair beam bending flat mirrors 60. The optical pulse 130 is modulated by the electro-optical modulator 80 into a short pulse train 140 as seen in FIG. 3. The pulse train 140 then goes into an analyzer 90, and then enters the amplifier 95. Amplifier 95 consists of flash lamp 30 and Nd-YAG laser rod 40. The short pulse train 140 is then amplified to pulse train 150 as seen in FIG. 4 and goes through the beam expander 100, and then the focusing optics assembly 110 to form beam 160. Beam 160 is then directed at the proximal end face 195 of the surgical needle 190 to form blind hole 198.

Figure 5:
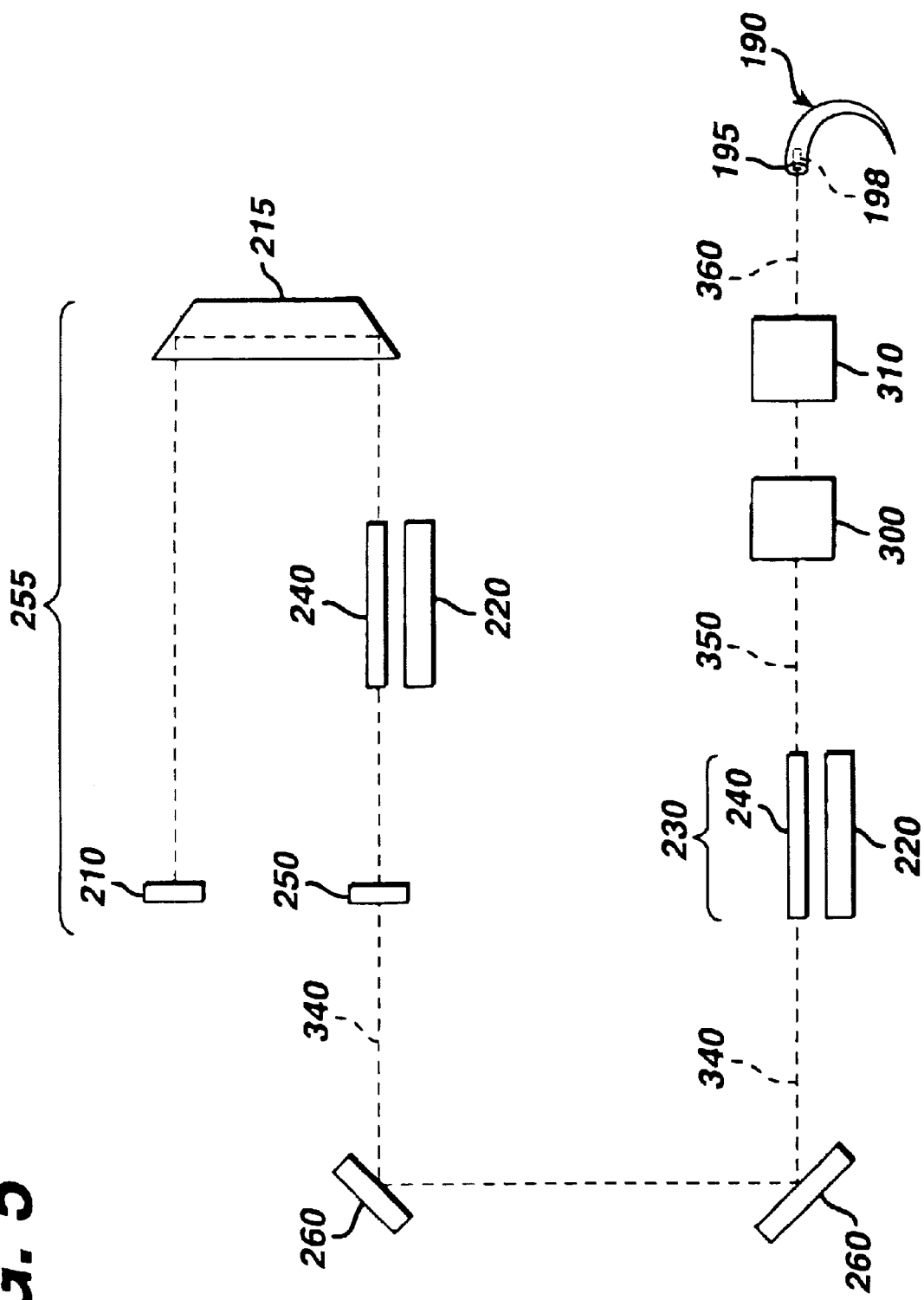
FIG. 5 is a schematic diagram illustrating a laser diode pumped Nd-YAG laser oscillator and amplified system of the present invention useful for drilling surgical needles.
Figure 6:
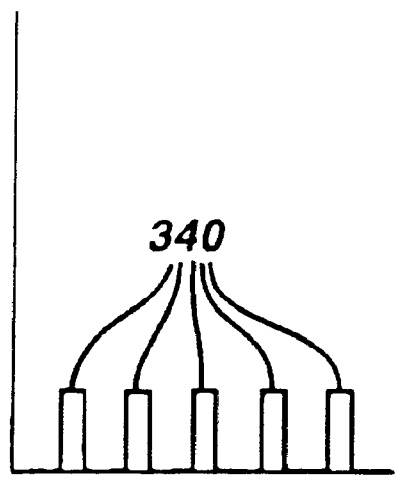
FIG. 6 is a schematic diagram illustrating a train of optical pulses produced by the laser diode pumped Nd-YAG laser oscillator of FIG. 5.
Figure 7:
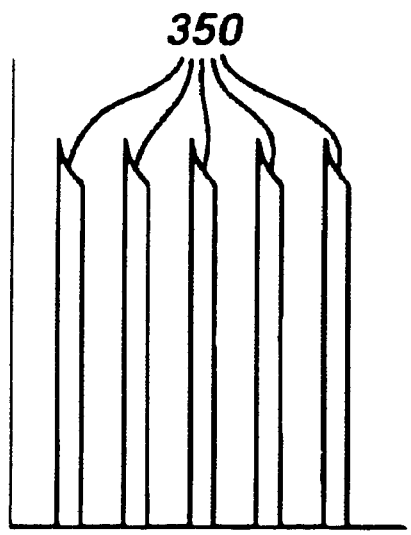
FIG. 7 is a schematic diagram illustrating the train of pulses of FIG. 6 after amplification.
Figure 8A:
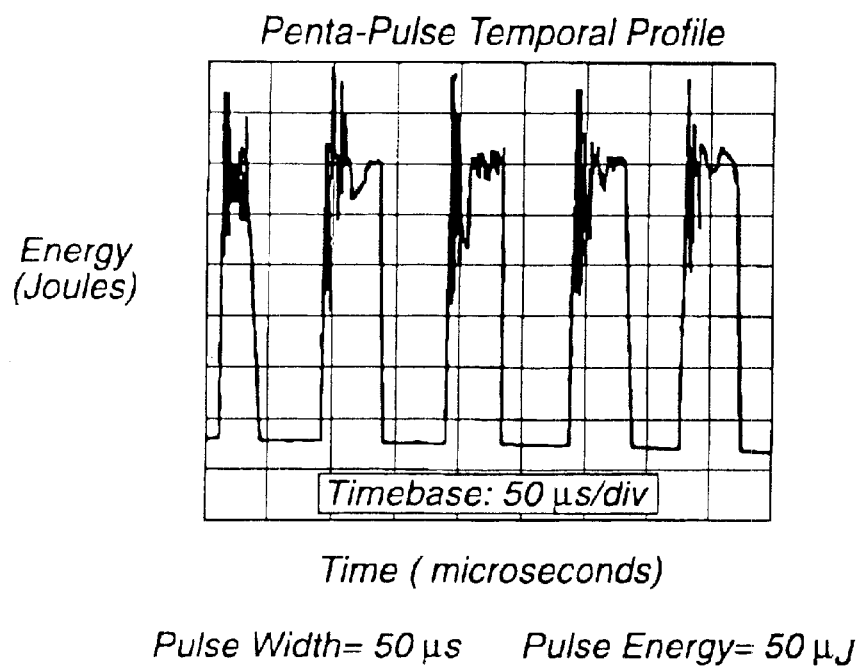
FIGS. 8A & B illustrate on an oscilloscope trace of optical pulses produced by the laser diode pumped Nd-YAG laser oscillator of FIG. 5.
Figure 8B:
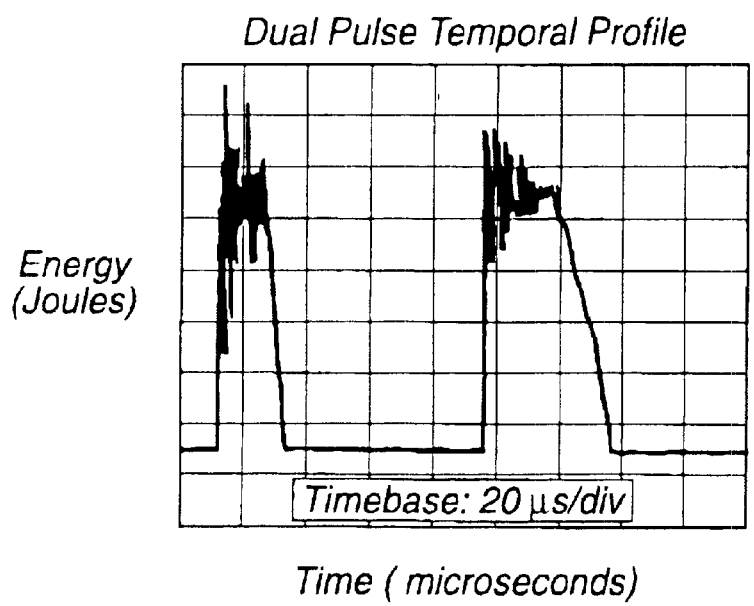

Referring now to FIG. 5, a schematic of a preferred embodiment of a laser diode pumped Nd-YAG laser system of the present invention useful for drilling surgical needles is disclosed. The system consists of a curved, 100% reflective rear mirror 210, a beam bending prism 215, a small diameter Nd-YAG rod 240, a group of high power laser diode arrays 220, and a partially transmitting outer coupler mirror 250. This establishes the laser oscillator 255. A solid state power supply (not shown in FIG. 5) drives the laser diode arrays for different powers, frequencies and pulse widths. The driving frequencies can range up to 10k Hz. The laser diode arrays 220 are made up of a number of diode bars. The diode arrays 220 emit radiation pulses in the narrow spectral width fitting to the small absorption bands of the Nd-YAG rod. The Nd-YAG rod 240 is optically pumped by the laser diode arrays 220 in the presence of the two mirrors 210 and 250, causing the laser oscillation to occur. The pulse width and pulse frequency of the Nd-YAG rod laser emission follows the pulse width and pulse frequency of the diode arrays. Nd-YAG optical pulses in the range of 5 microseconds to 100 microseconds can be produced. These pulses come in the form of a pulse train 340 as seen in FIG. 6. The pulse train 340 sequentially goes through a pair of beam bending flat mirrors 260 before it is sent to the amplifier section 230. Amplifier section 230 consists of an Nd-YAG rod 240 and a group of high power arrays 220. It should be noted that in both the laser oscillator 255 and laser amplifier 230, the laser diode arrays 220 pump the Nd-Yag rod 240 along the side. The power of the high powered laser diode bar 240 is in the range, preferably, of about 40 to 50 watts, and is sufficiently effective to produce the pulse train desired. Each array 220 can have "N" number of bars and these arrays can be arranged in different configurations around the Nd-YAG rod to illuminate the rod. The amplified pulse train 350 as seen in FIG. 7 is then sent to beam expander 300, and a focusing optics assembly 310 where the laser beam 360 finally is focused on the proximal end face 195 of surgical needle 190. When the amplified high power short pulses 360 are focused on the end face 195 of needle 190, they remove metal in the form of evaporation and plasma formation, which produces high quality blind holes 198.

The diode pumped Nd-YAG laser drilling systems of the present invention have many advantages over the flash lamp pumped systems of the prior art. Using the laser diode pulsed Nd-YAG laser drilling systems of the present invention, it is now possible to eliminate the optical polarizer, electro-optical modulator, analyzer, flash lamp and its associated power supplies and capacitor banks used in a conventional flash lamp pulsed system.

In addition, it is now possible to obtain higher beam quality due to the reduction of thermal lensing effect caused by excessive heat input to the rod by flash lamp. Laser beam alignment and maintenance are simpler and easier due to the elimination of the pulse modulating system of the prior art.

The laser drilling systems of the present invention have higher energy efficiency, and reduced laser downtime since it is no longer necessary to replace flash lamps.

The 100% reflective rear mirrors useful in the laser systems of the present invention include conventional, commercially available curved reflective mirrors such as those available from CVI Laser Optics Corp., Albuquerque, N. Mex., Lambda Research Optics Inc., Cerritos, Calif., and Coherent Auburn Group, Auburn, Calif. The size of the mirrors will preferably be about Ø0.5"×0.25" thick. The reflective mirrors function to create the lasing process.

The Nd-YAG laser rods useful in the laser systems of the present invention include conventional, commercially available small diameter rods such as 1.0% Nd-Yag. The size of the laser rods will be sufficient to effectively convert enough of the 808 nm pump light into 1064 nm lasing light. The size of the rods will typically be from about Ø0 2.5 mm to about Ø6.0 mm, more typically about Ø2.5 mm×100 mm to about Ø6.0 mm to 200 mm and preferably about Ø3.0 mm×140 mm to about Ø4.0 mm×140 mm. The laser rods function to convert pump light energy into lasing light energy. The laser rods are available from Litton Airtron Synoptcs, Charlotte, North Carolina as Part No. Nd:YAG 3×104 mm. The laser diode bars are available from Coherent, Inc. as Part No. ULPS156E/9/3.

The partially transmitting output coupler mirrors useful in the practice of the present invention include conventional, commercially available output coupler mirrors such as Ø0.5"×0.25" thick dielectrically coated substrates.

The coupler mirrors function to maintain the lasing process inside the resonator while at the same time allowing some of the resonator light to exit.

The laser diode arrays useful in the systems of the present invention include conventional, commercially available diode arrays such as radial arrays. The diode arrays function to generate 808 nm pump light energy. The diode arrays will typically consist of a plurality of laser bars. The laser bars are conventional, commercially available laser bars such as AlGaAs. The laser bars function to convert electrical energy into 808 nm optical energy.

The solid state power supplies useful to power the diode arrays include conventional, commercially available power supplies such as laser diode drive. The power supplies function to convert standard wall plug electrical power into pulsed electrical power. The capacity of the power supplies will be sufficient to effectively provide pulsed electrical power. The power will typically range from about 10 watts to about 500 watts, more typically about 50 watts to about 400 watts, and preferably about 100 watts to about 350 watts.

The beam bending flat mirrors useful in the laser systems of the present invention include conventional commercially available beam bending flat mirrors such as dielectrically coated glass substrates. The beam bending flat mirrors function to reflect laser light energy.

The beam expander useful in the practice of the present invention includes conventional, commercially available beam expanders such as the ones from CVI Laser Optics Corp. or Lambda Research Optics Inc. and Coherent Auburn Group. The beam expander functions to expand the diameter of the laser beam while at the same time collimating the laser beam.

The focusing optics assemblies useful in the practice of the method of the present invention includes conventional, commercially available optics assemblies such as 100 mm or 150 mm focusing lenses. The optics assembly functions to focus the laser light energy into a small spot.

As mentioned previously, the parts used in the laser systems of the present invention are commercially available. For example, the rear mirror can be purchased from JML Direct Optics in Rochester, New York as Part No. MPC14700/505, the prism may be purchased from JML Direct Optics as Part No. PDC 16120/104, while the output coupler mirror, the beam bending mirror, beam expander and focusing lens can be purchased form JML Direct Optics as Part Nos. CMN 11225/202/xxx, MCL 15100/505, 52340/104 and CLL 13745/104 respectively.

The laser beams used to drill surgical needles in the process of the present invention will have power, pulse frequency, and pulse width sufficiently effective to drill blind holes in metal surgical needles. The power of the beam will typically be about 5 watts to about 100 watts, more typically about 10 watts to about 50 watts, and preferably about 25 watts to about 45 watts. The pulse width of the beam will typically be about 5 microseconds to about 1 millisecond, more typically about 7 microseconds to about 200 microseconds, and preferably about 10 microseconds to about 100 microseconds. The frequency of the beam will typically be about single pulse to about 100 kHz, more typically about 1 kHz to about 50 kHz, and preferably about 1.5 kHz to about 10 kHz. The power of the beam is varied by varying the pulse energy and/or pulse frequency. The frequency of the beam is varied by the operator. The pulse width of the beam is varied by the operator.

Figure 9:
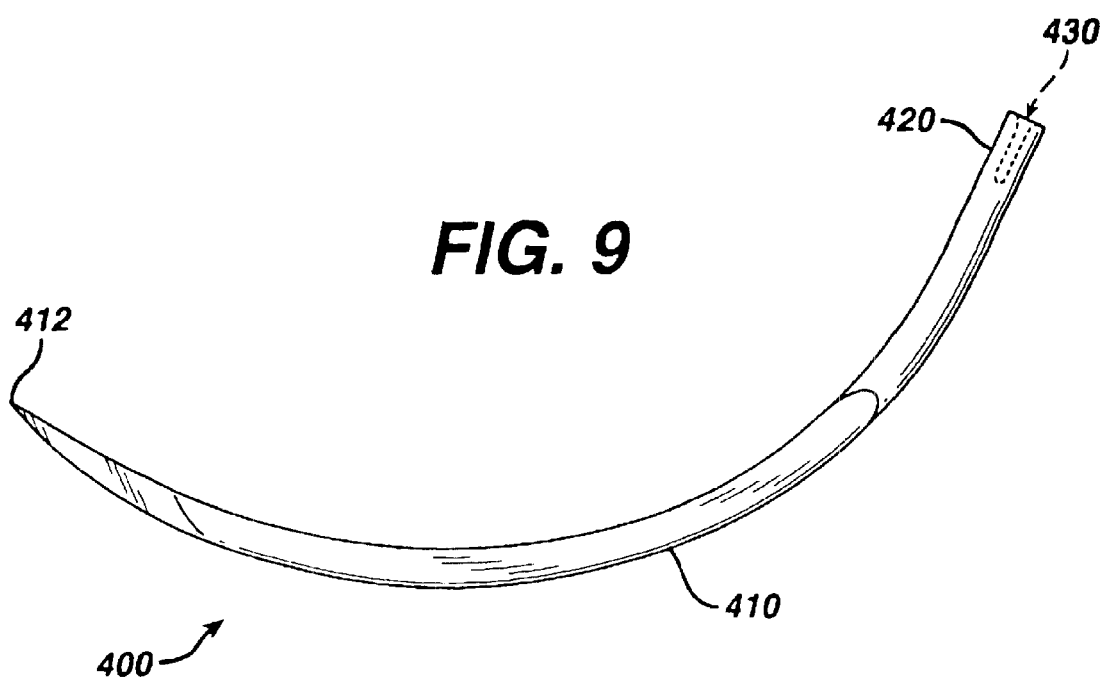
FIG. 9 is a perspective view of a surgical needle having a laser drilled chamfered bore hole.
Figure 10:
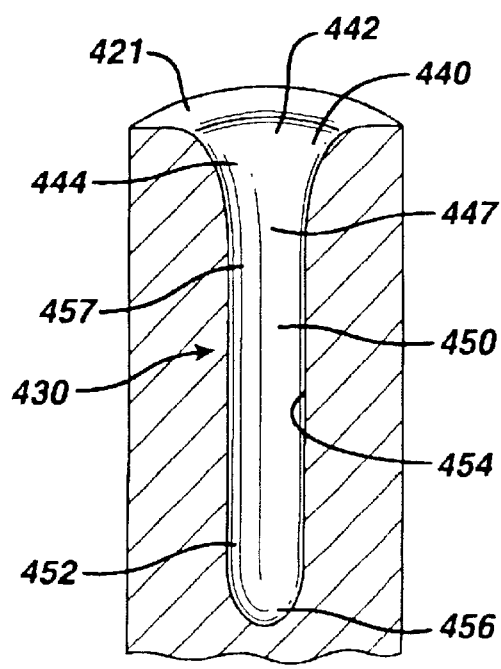
FIG. 10 is a partial cross-sectional view of the surgical needle of FIG. 10 illustrating the proximal end of the needle and the laser drilled chamfered bore hole.
Figure 11:
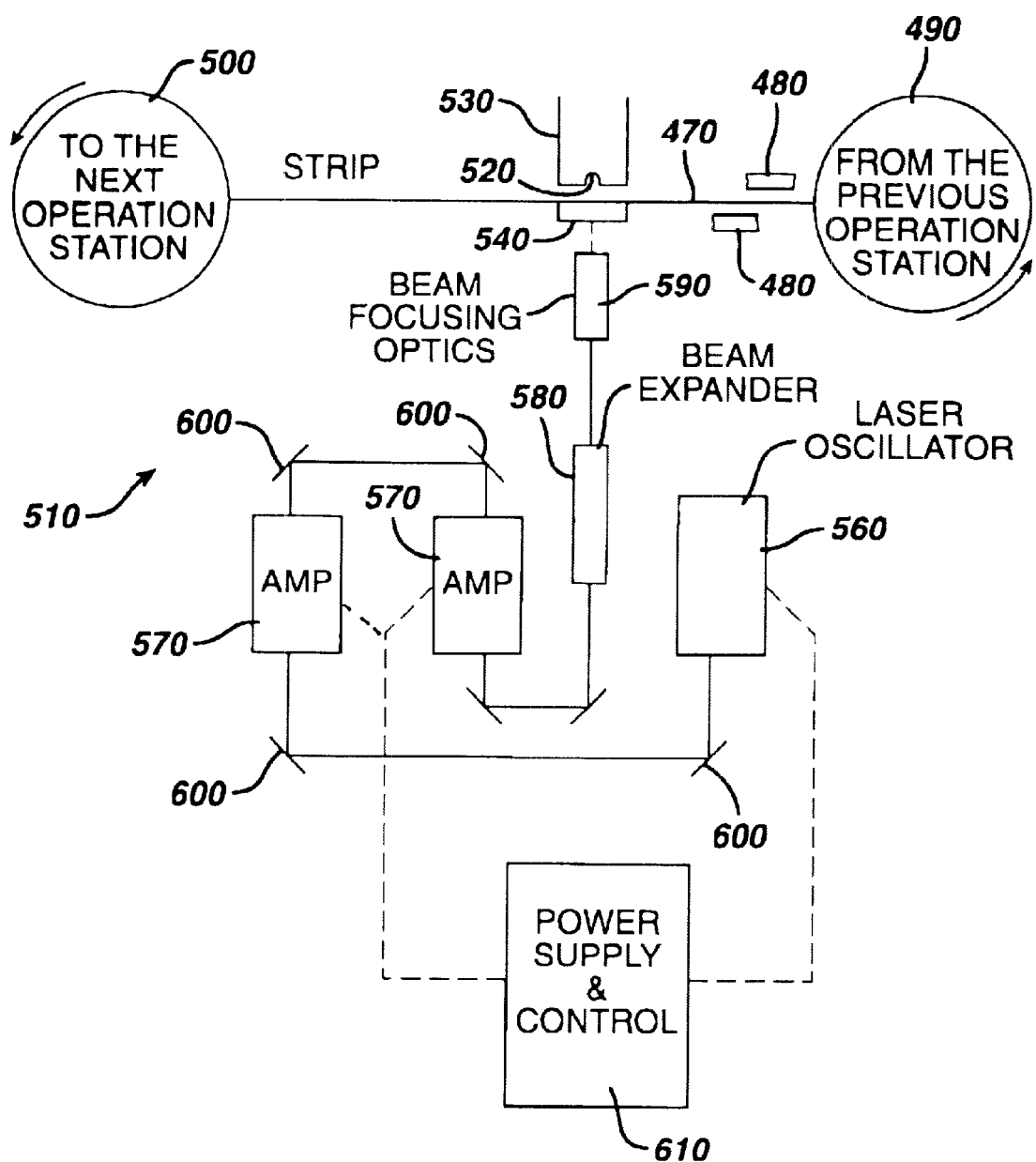
FIG. 11 is a schematic diagram of a laser drilling apparatus of the present invention useful to drill chamfered bore holes in surgical needles.

Referring now to FIGS. 9–11, a process of the present invention for laser drilling of chamfered bore holes in surgical needles is seen. A needle 400 having a laser drilled chamfered bore hole 430 is illustrated in FIGS. 9 and 10. The chamfered bore hole 430 is laser drilled by the laser drilling process of the present invention. The needle 400 is seen to be a conventional curved surgical needle having an elongated body 410, with distal piercing tip 412 and proximal end 420 having proximal end face 421. Proximal end 420 is seen to have the chamfered bore hole 430 extending therein. Chamfered bore hole 430 is seen to have chamfered cavity 440 and longitudinal bore hole 450. Chamfered cavity 440 is seen to be substantially hemispherically shaped, but may have other geometric shapes as well including square, rectangular or trapezoidal and the like and combinations thereof. Chamfered cavity 440 is seen to extend into proximal end 420. Cavity 440 has top opening 442 extending through proximal end face 421, inner walls 444 and bottom opening 447 in bottom 446. Bore hole 450 is seen to have cavity 452, side walls 454, distal blind bottom 456 and top opening 457 in communication with opening 447 of cavity 440. Such that, the distal end of a suture inserted into top opening 442 will extend through cavity 440, through openings 447 and 457 and into cavity 452 of bore hole 450.

The chamfered laser drilling process of the present invention is illustrated in FIG. 11. In the process illustrated, the needles 400 are mounted onto a carrier strip 470 that moves in linear tracks 480 from payout spool 490 to recoil spool 500. Although it is preferred to mount the needles 400 to a carrier strip 470, the chamfered laser drilling process of the present invention may also be performed using needles singly mounted to a needle die holder. While on the carrier strip 470, several optional operations at different stations may be performed prior to and subsequent to the chamfered laser drilling including but not limited to pull out (i.e., repositioning of the needle 400 along its long axis within the strip 470), needle cut off (removal of the tail portion of a needle 400 thus exposing an end surface of the needle 400 for drilling and chamfering), and bore hole 430 inspection are performed. However, these operations may be performed prior to placing the needles 400 onto the carrier strip 470, or after removal from the carrier strip 470 in the case of bore hole 430 inspection.

At the laser drilling station 510, each needle 400 is firmly held, by a die 530 in a die fixture 520, before a laser beam 540 hits the proximal end 420 of the needle 400. The laser beam 540, generated in the diode-pumped Nd-YAG oscillator 560, is reflected off of a beam bending flat mirror 600 and amplified by passing through two amplifier units 570 in series. The beam 540 then is reflected off of mirrors 600 and passes through the beam expander 580 and focusing optics 590 before it impacts the proximal end face 421 of the needle 400 to drill a hole. Sufficiently effective multiple pulses of either the same energy level or different energy levels are applied depending on the diameter and depth of the hole that is desired. The chamfer 440 is initially drilled in the proximal end 420 of needle 400 by the first laser beam pulse train 540 having sufficient energy and a sufficient duration to effectively drill out the chamfer cavity 440. The bore hole 450 is subsequently drilled in the proximal end 420 through the chamfer cavity 440 to create the chamfered bore hole 430 by a second laser beam pulse train 540. The second laser beam pulse train 540 has sufficient energy and a sufficient duration to effectively drill out the bore hole 420.

The amount of energy required to drill chamfer 440 will typically be less than the amount of energy required to drill the bore hole 450. The pulse width, pulse duration and the power (i.e., energy) of the laser beam pulse train 540 is controlled by the power supply and controller 610. These operations are performed one after another in one or two laser bursts. The combined maximum time required drilling the bore hole and its associated chamfer will vary with the process parameters and may be for example about 7 milliseconds. After the bore hole and its associated chamfer are formed, the strip moves the needle 400 in the linear tracks 480 to the next operation station or to the recoil spool 500. The laser pulse width range is typically about 5–25 microseconds, the current for the diodes in the oscillator and amplifiers ranges typically from about 20 to 60 amperes. The pulse frequency range is typically about 12.5–66 kHz. The maximum time for each laser burst is about 1 milliseconds. The controller 610 typically controls the laser drilling of the chamfered bore hole 430. Controller 610 is a conventional programmable central processing unit that consists of at least one microcontroller or microprocessor. The controller 610 has two modes of operation: single Pulse Mode (SPM) and Pulse Frequency Mode (PFM). In SPM the laser will deliver one burst of laser energy upon command. In Pulse Frequency Mode the laser will pulse at a selected frequency, for example 6 Hz with the shutter closed and will open the shutter upon command. The time between bursts can be adjusted to sufficiently effective, for example from about 5 milliseconds to about 15 milliseconds in 1 millisecond increments. The microcontroller or microcontrollers monitor and control the system to ensure reliable operation. The operating parameters can be adjusted by entering the desired settings through a membrane keypad located on the front panel of the central processing unit of controller 610. The central processing unit and microcontrollers also perform system diagnostics and load testing. At system power-up the central processing unit and microcontrollers of controller 610 perform initial system tests. During operation, the central processing unit and microcontrollers of controller 610 monitor several critical system parameters to ensure reliable system performance in an effective manner. The controller 610 is programmed to fire the laser with a burst containing one or several pulses. The first burst creates the chamfered cavity and typically has a duration of about 100 microseconds to about 1 millisecond, preferably about 500 microseconds. The controller 610 is also programmed to fire the laser with the second burst after completion of the first burst. The second burst contains several pulses and it creates the bore hole cavity. The second burst duration is preferably about 100 microseconds to about 1 millisecond, preferably about 800 microseconds. The controller 610 can also be programmed to produce one burst with the first pulse in the burst having different parameters than the other pulses in the burst, so that the first pulse make the chamfered cavity and the other pulses make the bore cavity. If desired, the controller 610 can be programmed to fire multiple bursts to produce the bore cavity and/or the chamfered cavity.

Surprisingly, utilizing the chamfered laser drilling process of the present invention, it is now possible to use a single diode-pumped laser to drill the chamfer and the bore hole of a chamfered blind bore hole.

Although this invention has been shown and described with respect to detailed embodiments thereof, it will be understood by those skilled in the art the various changes in form and detail thereof may be made without departing from the spirit and scope of the claimed invention.

What is claimed is:

1. A method of laser drilling surgical needles, the method comprising the steps of:

providing a diode pulsed laser Nd-YAG drilling system;

providing a surgical needle having a proximal end, a distal end, and a proximal end face:

producing a first beam of laser pulses having sufficient power to effectively drill a chamfer cavity in the proximal end of the surgical needle through the proximal end face;

directing the first beam of laser pulses onto the proximal end face of the proximal end of a surgical needle to produce a chamfer cavity having a distal bottom;

producing a second beam of laser pulses having sufficient power to effectively drill a blind bore hole in the proximal end of the surgical needle;

directing the second beam of laser pulses onto the distal bottom of the chamfer cavity to produce a chamfer cavity having a distal bottom, wherein said blind bore hole is in communication with the chamfer cavity.

2. The method of claim 1 wherein the diode pulsed laser drilling system comprises:

a curved rear mirror;

a first Nd-YAG rod;

a plurality of high power laser diode arrays;

a partially transmitting output coupler mirror;

a solid state power supply to drive the diode arrays;

first and second beam bending flat mirrors;

a second Nd-YAG rod;

a second plurality of high power laser diode arrays;

a beam expander;

a focusing optics assembly; and, a controller.

3. The method of claim 1, wherein the first beam has a power of about 0.45 kilowatts to about 2.5 kilowatts.

4. The method of claim 1 wherein the first beam has a pulse width of about 5 microseconds to about 10 microseconds.

5. The method of claim 1, wherein the frequency of the first beam is from about 1 kHz to about 20 kHz.

6. The method of claim 1, wherein the second beam has a power of about 0.58 kilowatts to about 3.2 kilowatts.

7. The method of claim 1 wherein the second beam has a pulse width of about 5 microseconds to about 20 microseconds.

8. The method of claim 1, wherein the frequency of the second beam is from about 1 kHz to about 30 kHz.

* * * * *